United States Patent
Kessler

(10) Patent No.: US 7,628,771 B2
(45) Date of Patent: *Dec. 8, 2009

(54) SECUREMENT DEVICE FOR INDWELLING CATHETERS OR INTRODUCERS

(75) Inventor: Alan Kessler, Los Angeles, CA (US)

(73) Assignee: Maddoc Medical Products, Inc., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/687,583

(22) Filed: Mar. 16, 2007

(65) Prior Publication Data

US 2007/0173769 A1 Jul. 26, 2007

Related U.S. Application Data

(62) Division of application No. 10/789,892, filed on Feb. 26, 2004, now Pat. No. 7,204,827.

(51) Int. Cl.
*A61M 5/32* (2006.01)

(52) U.S. Cl. ........................ 604/174; 604/180

(58) Field of Classification Search ................ 604/174, 604/177, 179–180, 344–345; 128/DIG. 6, 128/DIG. 26; 606/232
See application file for complete search history.

(56) References Cited

U.S. PATENT DOCUMENTS

| | | | |
|---|---|---|---|
| 4,778,446 A | 10/1988 | Jensen | |
| 4,966,590 A | 10/1990 | Kalt | |
| 5,147,322 A | 9/1992 | Bowen et al. | |
| 5,188,609 A * | 2/1993 | Bayless et al. | 604/180 |
| 5,224,935 A | 7/1993 | Hollands | |
| 5,282,463 A | 2/1994 | Hammersley | |
| 5,314,411 A | 5/1994 | Bierman et al. | |
| 5,637,098 A | 6/1997 | Bierman | |
| 5,643,216 A | 7/1997 | White | |
| D393,903 S | 4/1998 | Bierman | |
| 5,792,115 A | 8/1998 | Horn | |
| 5,855,591 A | 1/1999 | Bierman | |
| 6,117,163 A * | 9/2000 | Bierman | 606/232 |
| 6,213,979 B1 | 4/2001 | Bierman | |
| 6,582,403 B1 | 6/2003 | Bierman et al. | |
| 7,204,827 B2 * | 4/2007 | Kessler | 604/180 |

OTHER PUBLICATIONS

International Search Report for Application No. PCT/US05/05333, completed Dec. 1, 2005.

* cited by examiner

*Primary Examiner*—Nicholas D Lucchesi
*Assistant Examiner*—Theodore J Stigell
(74) *Attorney, Agent, or Firm*—Knobbe, Martens, Olson & Bear LLP

(57) ABSTRACT

A securement device for Indwelling Catheters or Introducers having a pad with an adhesive backing for securement to the skin of a patient. A base is mounted on the pad having one or more spaced holes therethrough with an elongated strand extending through said hole or holes. The strand may be wrapped around or passed through a connector mounted on the base and the free end(s) thereof may be tied to the strand or to another strand arising from the base.

30 Claims, 6 Drawing Sheets

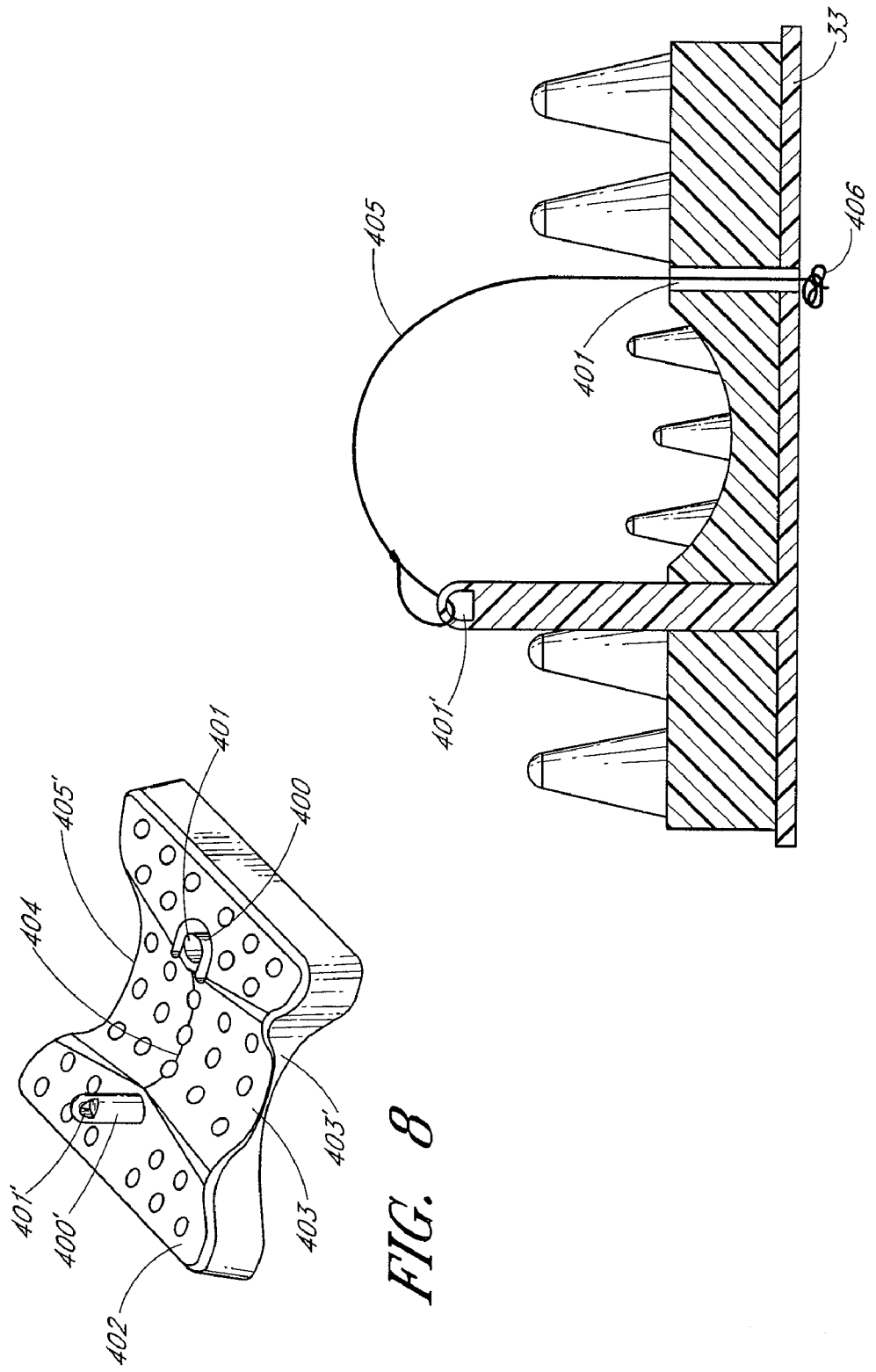

SECUREMENT DEVICE FOR INDWELLING CATHETERS OR INTRODUCERS

RELATED APPLICATIONS

This application is a divisional of application Ser. No. 10/789,892, filed Feb. 26, 2004, and titled SECUREMENT DEVICE FOR INDWELLING CATHETERS OR INTRODUCERS, now issued as U.S. Pat. No. 7,204,827, which is hereby incorporated by reference in its entirety.

BACKGROUND OF THE INVENTION

1. Field of the Invention

The invention relates to securement devices; and, more particularly, to anchoring systems for anchoring or securing medical articles to the body of a patient.

2. Description of the Related Art

It is well known in the treatment of patients to introduce fluids and medications directly into the bloodstream. Many devices are known for quickly and easily securing a catheter, tube, etc. to the skin of a patient without suturing.

Various devices have been suggested in the past which require carefully machining of parts of said medical articles to form apertured ears or tabs to anchor the securement strands to a catheter or the like. Certain securement devices require specially manufactured strands or posts with protuberances. Other securement devices are specifically adapted to a particular type of catheter or the like thus not easily accommodating catheters of different configurations.

These devices do not put tension on the strands holding the catheter in place.

There is a need for a securement device for percutaneous sheath introducers and other medical devices which uses flexible strands for securement means thus allowing versatility and flexibility and does not require careful and expensive machining of the medical articles to be secured. Such a device should easily accommodate catheters of varying configurations.

SUMMARY OF THE INVENTION

It is an object of this invention to provide a securement device for indwelling catheters or introducers and other medical articles which uses strands of material as the securement means of tying a catheter or the like in position on the body of a patient.

It is another object of this invention to provide such a device having a base secured to a pad adapted to be secured to the body of a patient, the base holding a catheter or the like in a firm fixed position on the base.

It is still another object of this invention to carry out the foregoing objects placing tension on the strands holding a catheter or the like in place on the base.

These and other objects are preferably accomplished by providing a pad having an adhesive backing for securement to the skin of a patient. A base is mounted on the pad having a one or more holes therethrough with an elongated strand(s) extending down through said hole or holes. The strand may be wrapped around a connector mounted on the base and tied to itself or two or more such strands, the free ends thereof tied to secure the connector to the base.

BRIEF DESCRIPTION OF THE DRAWINGS

FIG. 8 is a view similar to FIG. 5 showing still another modification of the base of FIG. 1; and FIG. 9 is a side view, in section, of the base of FIG. 8.

DETAILED DESCRIPTION OF THE PREFERRED EMBODIMENT

Figure 1:
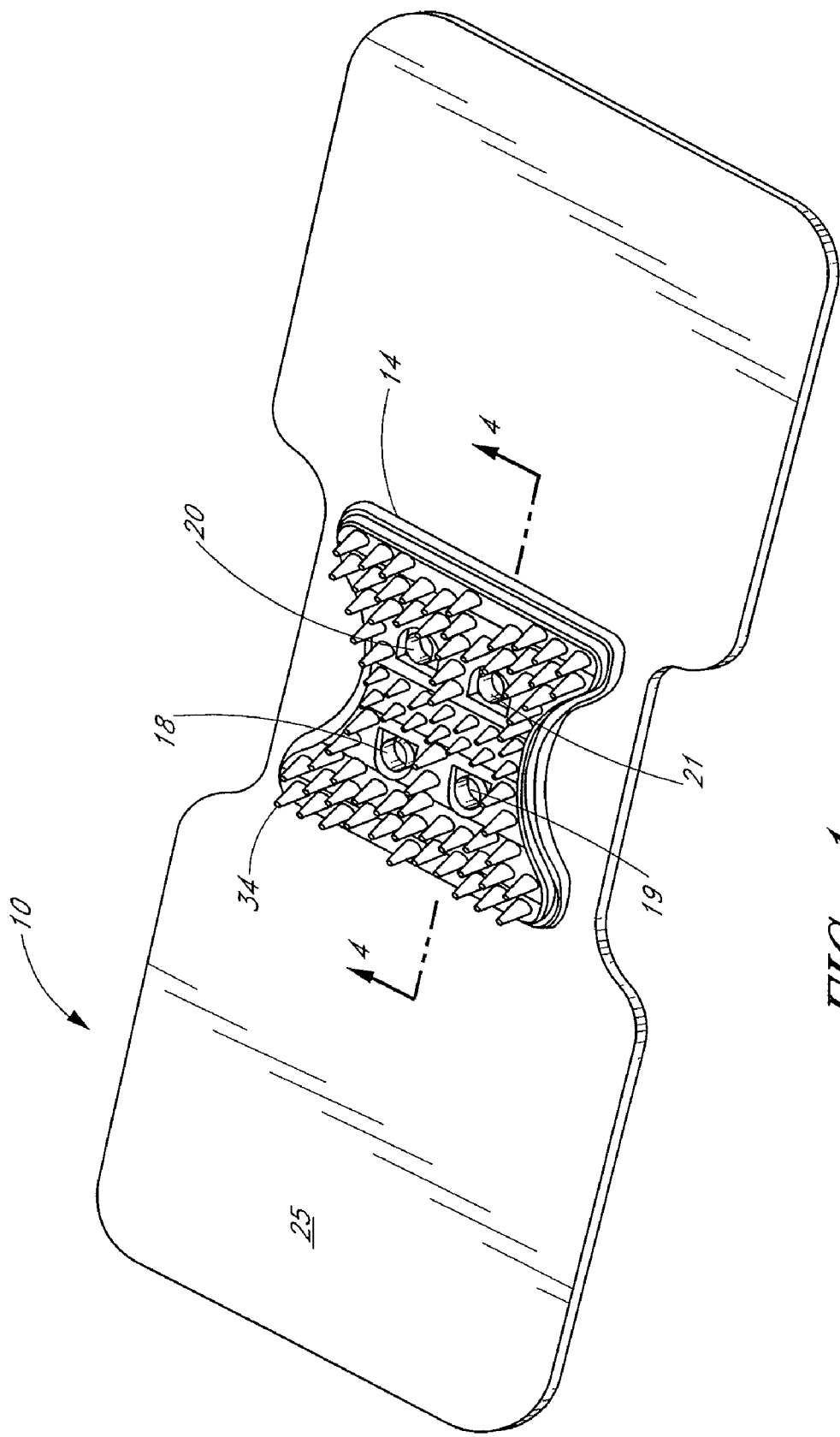
FIG. 1 is a perspective view of a securement device in accordance with the teachings of the invention.
Figure 2:
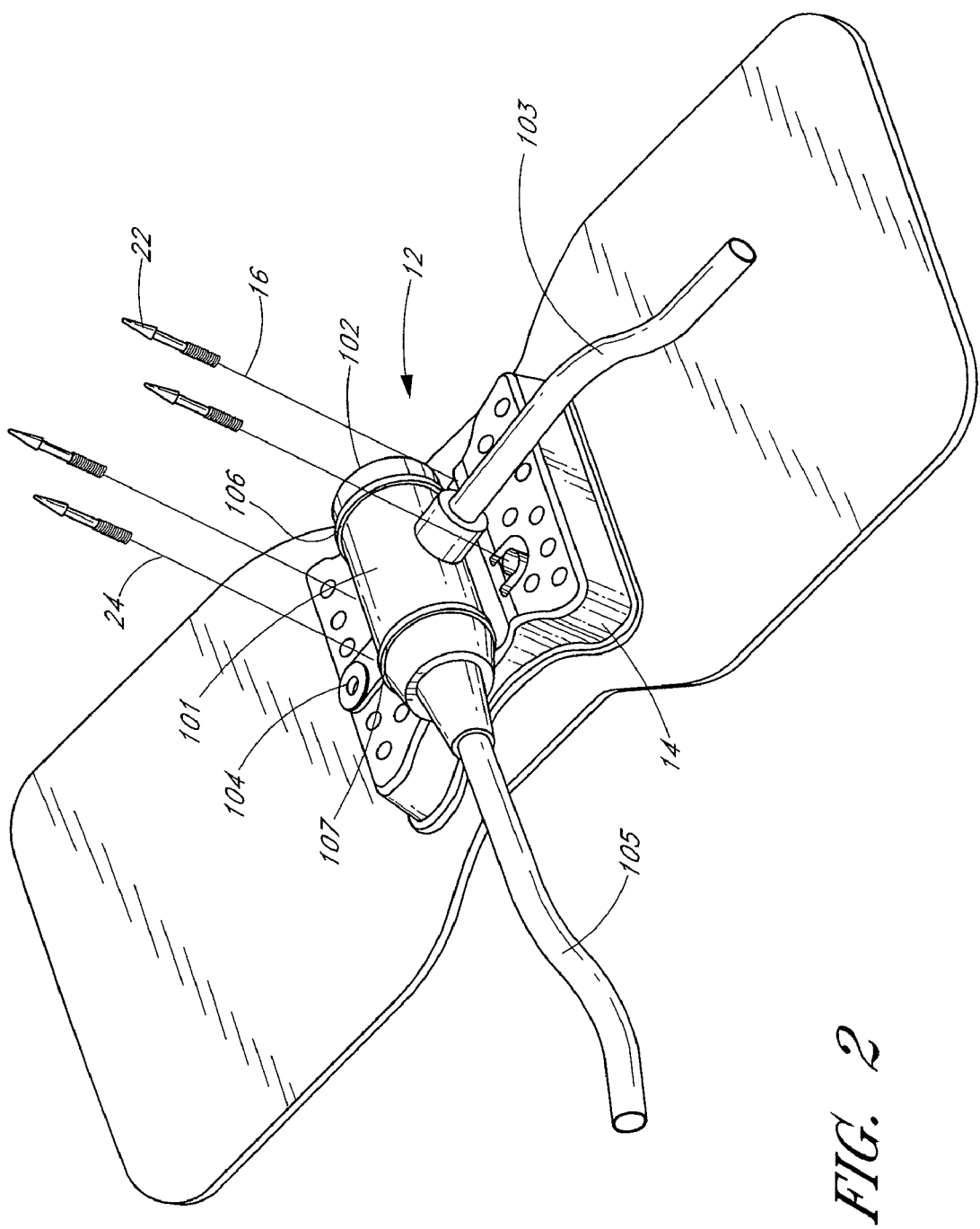
FIG. 2 is a perspective view of the device of FIG. 1 showing a connector mounted thereto.

Referring now to FIG. 1, a securement device 10 is shown adapted to be used in connection with a catheter type conventional fluid line connector 12 (FIG. 2). It is to be understood that, although illustrated as to be used with a catheter, the securement device 10 herein can be used with other types of medical devices or articles such as, for example, CVCs, PICCs, Foley catheters, hemodialyses catheters, surgical drainage tubes, feeding tubes, chest tubes, nasogastric tubes, or with wires or cables coupled to external or implanted electronic devices or sensors. Thus, as used herein, "medical devices or articles" means generally any suitable or generic type catheter, fluid supply and drainage line, connector, adaptor, electrical wire or cable, etc. which may be retained by the securement device herein and used to introduce fluids or allow drainage or the like through medical devices into or out of the patient's body.

Figure 3:
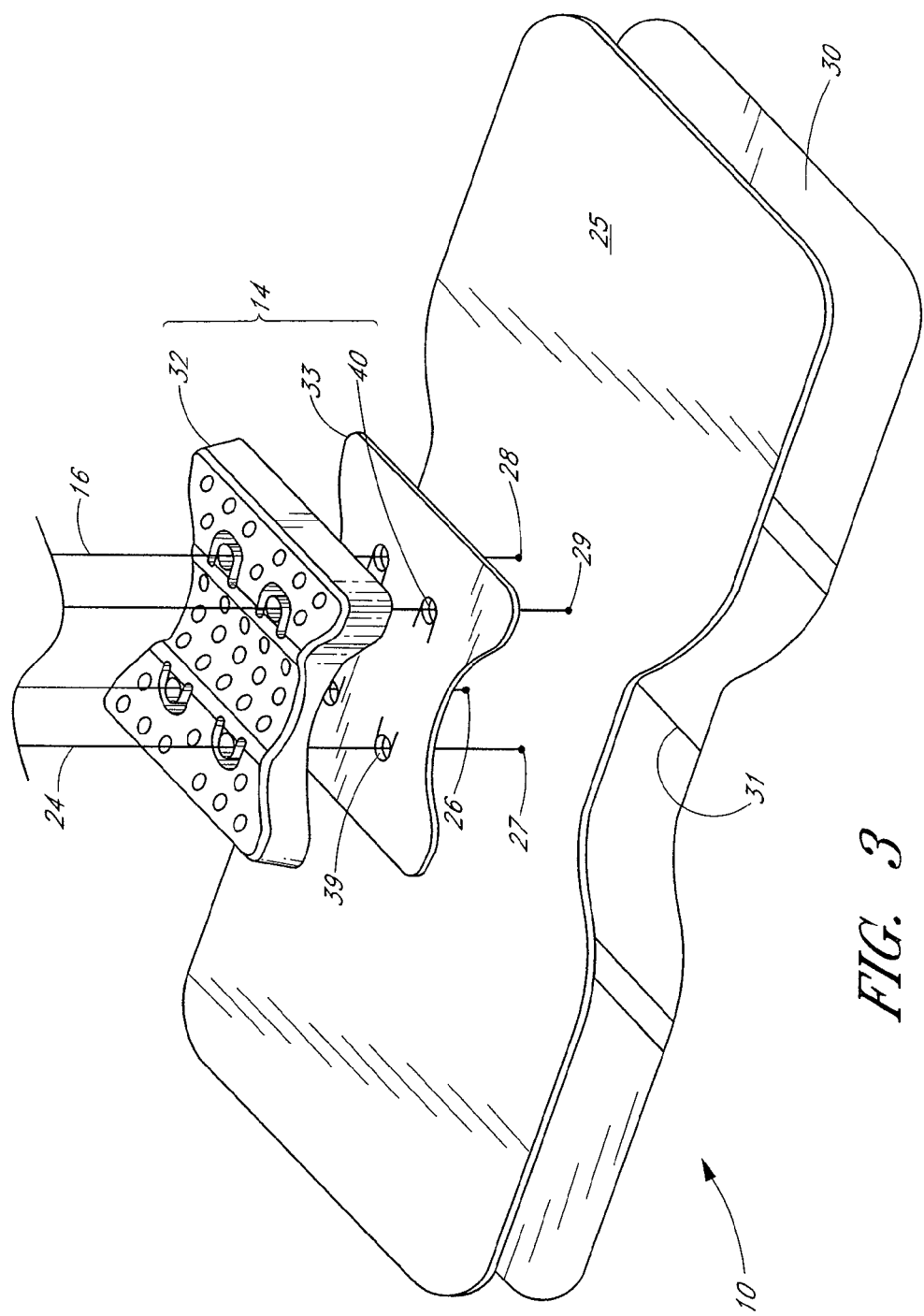
FIG. 3 is an exploded view of the base, pad and backing of the device of FIGS. 1 and 2 illustrating a pair of flexible strands extending through aligned holes in the base and pad.

Securement device 10 thus includes a base 14 adapted to be secured to an anchor pad 25 (FIG. 3) and one or more filaments or strands, such as 2 strands 16, 24 (FIGS. 2 and 3) that extend from base 14.

Base 14 is secured to anchor pad 25 which is configured as shown (generally referred to as a butterfly configuration) and secured thereto in any suitable manner, such as by a solvent bond adhesive.

One or more holes 26 through 29 (FIG. 3) are provided through pad 25 aligned with holes 18 to 21 (FIG. 1), respectively, in base 14.

In the example shown, two such strands 16, 24 are shown adapted to be fed through holes 18 through 21 (FIG. 1) in base 14 and aligned holes 26 to 29 in pad 25. Thus, one strand 16 may be fed alone through aligned holes 19, 27 and up through aligned holes 29, 21 and the other strand may extend down through aligned holes 18, 26 and up through aligned holes 28, 20. Of course, any suitable number of strands and holes may be used.

Each strand 16, 24 may have a pointed distal end 22 (FIG. 2) which may be hardened, such as a lacquered tip. Any suitable strand length may be used depending on the application.

The anchor pad 25 may be of flexible material as is well known in the art and may comprise a layer of a closed cell, low-density polyethylene foam and a bottom layer of a medical grade adhesive. A removable paper or plastic backing 30 (see FIGS. 3 and 4), conforming to anchor pad 25, covers the bottom adhesive surface of pad 25 before use. The backing 30 is of a suitable material to resist tearing and may be divided into a plurality of pieces, such as 2, for ease in attachment of pad 25 to the patient's skin. Preferably, backing 30 is of 2 pieces, adhesively attached to the bottom of pad 25 at its center 31 (FIG. 3) having end portions unattached to pad 25 which can be pulled apart to expose one half of the adhesive pad at a time. Other means may be used, such as a single piece of backing which has a portion extending beyond the edge of pad 25 to ease removal as is well known in the art.

Base 14 is comprised of two parts (FIG. 3), an upper support base 32 secured to a lower part or support plate 33 which in turn is secured to pad 25. Plate 33 is preferably of a polycarbonate material glued or otherwise secured to pad 25.

Support base 32 may be of a suitable molded polymeric material having an upper surface covering with a plurality of upstanding generally conically shaped protrusions 34 (FIG. 4) extending upwardly therefrom.

A spring beam 35 is mounted internally or integrated into support plate 33 for reasons to be discussed.

Holes 18 through 21 in support base 32 are aligned with like holes (FIG. 3) through support plate 33 which holes are also aligned with holes 26 to 29, as previously discussed.

Figure 4:
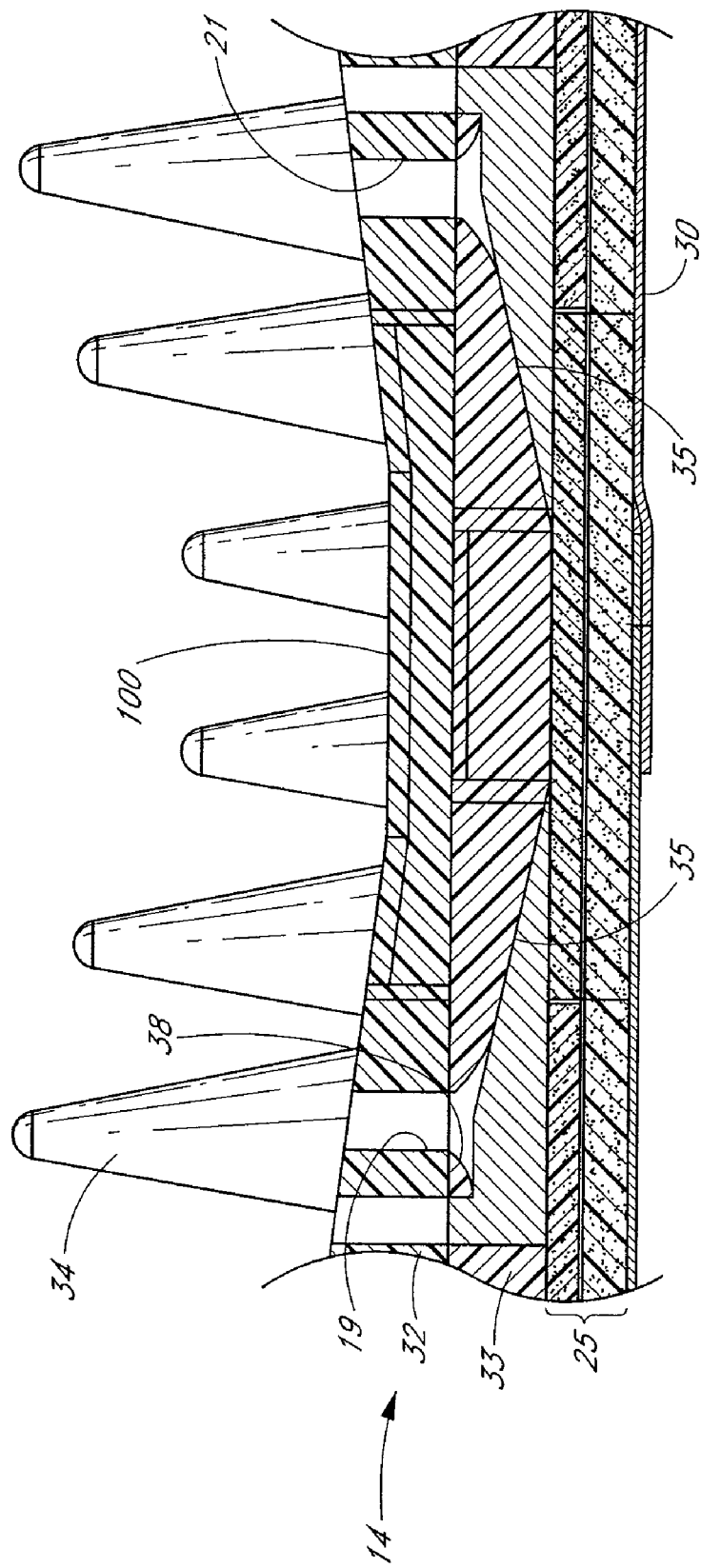
FIG. 4 is a side view, in section, illustrating the interior structure of the base of the device of FIGS. 1 to 3.

As seen in FIG. 4, holes 18 to 21 are circular through the beam 35. The edges of each hole are radiused (see radiused wall portion 38—FIG. 4).

As seen in FIG. 4, the protrusions 34 may vary in overall height and are preferably of a suitable elastomeric material. Strands 16, 24 may be of any suitable material, such as silk. Silk is less likely to slide during use. Thus, strand 24 extends through hole 19 in upper support base 32, down through aligned hole 39 in support plate 33, about the underside of spring beam 35 (which thus provides tension when strand 24 is tied), up through hole 40 in support plate 33, and through aligned hole 21 in support base 32 and upwardly as shown. Alternatively, all strands could extend up and be knotted at the respective holes 19, 21 or glued to the underside of the support plate 33.

As discussed, any suitable materials may be used, such as a fabric material for pad 25 with a base 14 of polycarbonate or similar material glued to pad 25. The radiused edges 38 of the holes eliminate sharp cutting edges. Strands or sutures 16, 24 may be No. 1 braided silk sutures. Support base 32 may be of any suitable polymeric material, such as a material of about 35A Durometer.

As seen in FIG. 4, upper support base 32 is slightly concave at its middle 100.

Looking at FIG. 2, the connector 12 has a main hub portion 101 having an inlet port 102 at one end for insertion of a catheter (not shown) therein and an elongated tubular portion 103 extending therefrom for fluid instillation. Hub portion 101 also has an apertured ear 104 on one side of the hub portion 101 and a flexible inlet tube 105 fluidly coupled to hub portion 101 for introducing fluids and directing an inserted catheter or wire therein, as is well known in the art. Of course, any suitable connector or catheter configuration may be used.

As seen in FIG. 2, connector 12 rests in the middle or concave portion 100 of upper support base 32. The protrusions 34 assist in holding the connector 12 in position. The strands 16, 24 extend through the aligned holes in upper support base 32 and lower support plate 33 and under beams 35.

Connector 12 may have one or more spaced annular grooves, such as grooves 106, 107 (FIG. 2). Strands 16, 24 may be tied to connector 12 in any suitable manner. For example, strand 16 may first be extended through the hole in apertured ear 104, then wrapped around groove 106 and the free ends tied. Strand 24 may be wrapped around groove 107 and the free ends tied. The overall length of one side of each strand may be easily adjusted to accommodate tying.

Although a particular type of connector is disclosed, having annular grooves, obviously any suitable type of connector may be used as long as strands 16, 24 can be wrapped around or through the holes and tied. The hardened ends 22 allow easy insertion through the aligned holes and the apertured ear.

The concave center 100 of upper support base 32 acts as an anti-roll channel for connector 12. This also prevents folding of the base 32 in the center.

Although 2 strands 16, 24 may be used to tie connector 12 to base 32, obviously one may be used. Thus, at least one strand is sufficient utilizing the teachings of the invention.

Figure 5:
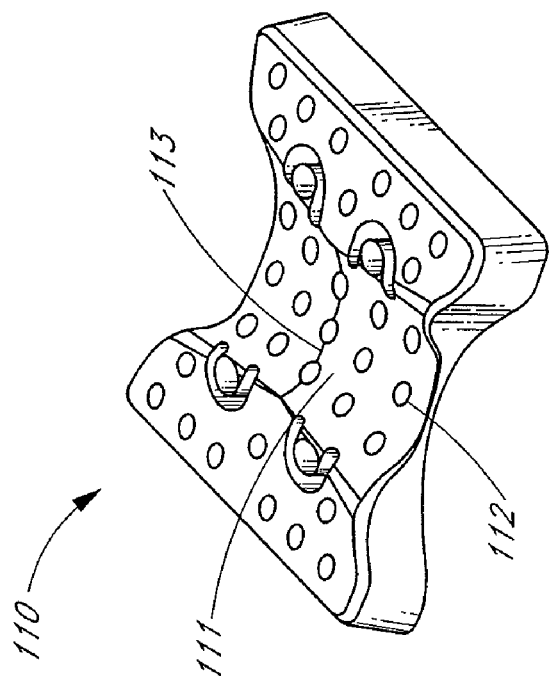

In a further embodiment of the invention, wherein like numerals refer to like parts of FIGS. 1 to 4, as seen in FIG. 5, base 110 otherwise identical to base 14, may have the upper surface 111 of upper support base 112 slightly raised, at its center 113, so that when connector 12 is secured in position, the inlet port 102 is in a slightly elevated position for easy insertion of a catheter into a connector mounted thereon (not shown).

Figure 6:
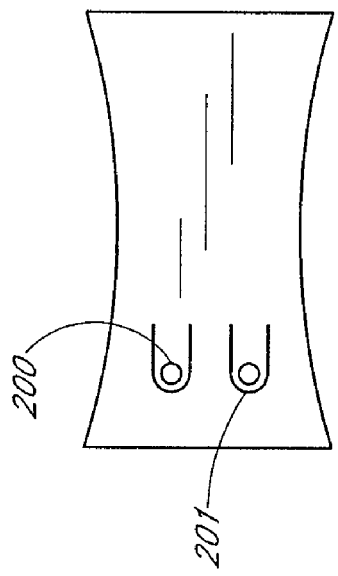
FIGS. 5 and 6 are top plan views of two different modifications of the base alone of the device of FIGS. 1 to 4.

Circular holes with radiused sides have been disclosed, as seen in FIG. 6, wherein like numerals refer to like parts of FIGS. 1 to 4, the holes for passage of the strands therethrough may include hole portions 200 extending through tabs or ears 201 which may be cut out of the support base and support plate or a single structure comprising both support base and support plate as disclosed below. The hole portions 200 communicate with aligned holes through the remaining portions of the base 14. The tabs 201 will thus flex slightly when the strands are pulled through the hole portions 200 and thereby exert a downward force through the strand on the connector once the strands are tightened around and/or over the connector. An upward force on the tabs forces the support base and plate to contour around the connector and thus prevents rolling of the device on the base.

Figure 7:
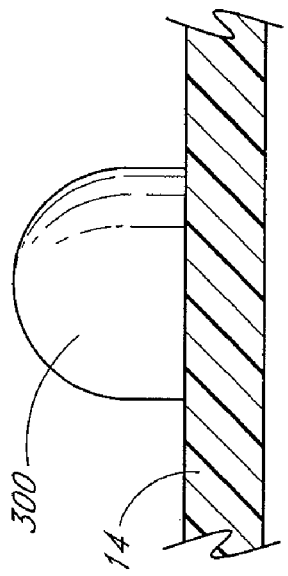
FIG. 7 is a perspective view of a portion of another embodiment of the base of FIG. 1.

In still another embodiment of the invention, as seen in FIG. 7 wherein like numerals refer to the embodiment of FIG. 1, base 14 may have hemispherically shaped protrusions, such as protrusions 300, extending upwardly therefrom instead of conically shaped protrusions. Also, as seen in FIG. 8, wherein like numerals refer to like parts of FIG. 1, tabs 400, 400' with holes 401, 401', respectively, therethrough, similar to tabs 201 and holes 200 in FIG. 6, may be provided on the upper surface of base 402. The area 403 is concave but raised slightly at the midpoint 404 thereof to provide a ramp for a connector or the like. That is, the area 403 may slope upwardly from one side 403' to midpoint 404, then slope downwardly from midpoint 404 to the other side 405'. In this embodiment, a single strand 405, otherwise identical to strands 16, 24, FIG. 9, may extend up through one hole 401, knotted on the underside of the lower support plate 33, as at knot 406, extend through hole 401 in the tab 400 as shown, then extends through hole 401' in post 400' and tied back upon itself, thus retaining a connector or the like (not shown).

The strands may be of silk or any flexible material that is substantially non-extendible about its long axis. The flexible beam 35 conforms to the shape of a connector mounted on the base and creates and maintains tension in the strands so as to keep any knots tight and pulls or presses the connector into the conforming surface preventing rolling. Also, beam 35 may be integral with plate 33 and base 32 with the hardness of the securement base 14 varying from the top to bottom thereof or of uniform hardness to allow both the cushioning/conforming effect of said base and the springlike character of said plate.

Although a particular embodiment of the invention is disclosed, variations thereof may occur to an artisan and the scope of the invention should only be limited by the scope of the appended claims.

What is claimed is:

1. A securement system for a medical article having a longitudinal axis, the system comprising:
   a flexible anchor pad having an adhesive bottom surface and a top surface;
   a retainer having a base and a plurality of protrusions, said base comprising an upper support base supported at least in part by a lower support plate, said lower support plate being secured to said top surface, said plurality of protrusions extending from said base and contacting said medical article at least two locations along the longitudinal axis of the medical article at least when said medical article is secured by said retainer; and
   a strand coupled to said retainer and having a free end, said free end being configured to be tied about a portion of said medical article and secured relative to said retainer, wherein said plurality of protrusions vary in overall height, and wherein said variation in height defines a concave upper surface for receiving said secured portion of said medical article.

2. the device of claim 1, wherein at least one of said plurality of protrusions is conically shaped.

3. The device of claim 2, wherein said at least one protrusion comprises a wide base portion at its connection to said base and extends upwardly to a rounded tapered end.

4. The device of claim 1, wherein said plurality of protrusions extends upwardly from said base.

5. The device of claim 1, wherein said concave upper surface is disposed in substantially the middle of the base.

6. The device of claim 1, wherein at least said lower support plate comprises polycarbonate material.

7. The device of claim 1, wherein at least said lower support plate comprises a plastic material.

8. The device of claim 1, wherein said upper support base comprises a polymeric material.

9. The device of claim 1, wherein said pad comprises a fabric material overlaid by a hydrocolloid adhesive material.

10. The device of claim 1, wherein said strand comprises a flexible material.

11. The device of claim 1, wherein said base has at least one hole extending therethrough, said strand extending through said hole.

12. The device of claim 11, wherein said hole extends through said upper support base and said lower support plate.

13. The device of claim 1 further comprising a biasing member embedded in said lower support plate, said strand being coupled to said biasing member.

14. The device of claim 13, wherein said biasing member is integral with said lower support plate and substantially conforms to the shape of said lower support plate.

15. The device of claim 14, wherein said biasing member creates and maintains tension on said strand when said strand is secured relative to said retainer.

16. The device of claim 1, wherein one of said at least two locations is offset in a direction perpendicular to the longitudinal axis from the other one of said at least two locations.

17. The device of claim 1, wherein said at least two locations are aligned with the longitudinal axis.

18. A securement device for a medical article comprising:
   an anchor pad;
   a plurality of protrusions being elastically deformable and having contact surfaces;
   a lower support, at least a portion of said lower support being disposed between said anchor pad and at least a portion of said plurality of protrusions, said portion of said lower support being harder than said portion of said plurality of protrusions;
   a strand having a free end configured to be tied about a portion of said medical article, said free end being securable relative to said lower support at least when said medical article is secured against said contact surfaces; and
   a biasing member, at least a portion of said biasing member being disposed below said plurality of protrusions and having a generally fixed base and a deflectable beam section that flexes relative to said fixed base.

19. The device of claim 18, wherein said portion of said lower support produces compressive stresses within said portion of said plurality of protrusions that bear against said portion of said medical article when said medical article is secured against said contact surfaces.

20. The device of claim 18, wherein said securement device increases in hardness from said contact surfaces to said anchor pad.

21. The device of claim 20, wherein said increase in hardness occurs at the interface of said plurality of protrusions and said lower support.

22. The device of claim 18, wherein said plurality of protrusions is comprised of a polymeric material that has a Shore A hardness of no greater than 35A durometer.

23. The device of claim 18, wherein said lower support is comprised of a first material and the plurality of protrusions is comprised of a second material, the second material being softer than the first material.

24. The device of claim 23, wherein said first material is a polycarbonate.

25. The device of claim 23, wherein said second material is a polymeric material.

26. A securement device for a medical article comprising:
   an anchor pad;
   a plurality of protrusions being elastically deformable and having contact surfaces;
   a lower support, at least a portion of said lower support being disposed between said anchor pad and at least a portion of said plurality of protrusions, said portion of said lower support being harder than said portion of said plurality of protrusions, wherein said lower support is comprised of a first material and the plurality of protrusions is comprised of a second material, the second material being softer than the first material; and
   a strand having a free end configured to be tied about a portion of said medical article, said free end being securable relative to said lower support at least when said medical article is secured against said contact surfaces.

27. The device of claim 26, wherein said portion of said lower support produces compressive stresses within said portion of said plurality of protrusions that bear against said portion of said medical article when said medical article is secured against said contact surfaces.

28. The device of claim 26, wherein said plurality of protrusions is comprised of a polymeric material that has a Shore A hardness of no greater than 35A durometer.

29. The device of claim 26, wherein said first material is a polycarbonate.

30. The device of claim 26, wherein said second material is a polymeric material.

* * * * *